(12) United States Patent
Okuro et al.

(10) Patent No.: US 7,282,605 B2
(45) Date of Patent: Oct. 16, 2007

(54) OPTICALLY ACTIVE 2-ALLYLCARBOXYLIC ACID DERIVATIVE AND PROCESS FOR PRODUCING THE SAME

(75) Inventors: Kazumi Okuro, Takasago (JP); Susumu Amano, Takasago (JP); Noriyuki Kizaki, Takasago (JP); Teruaki Takesue, Takasago (JP); Masaru Mitsuda, Takasago (JP); Noriyuki Ito, Takasago (JP); Yoshihiko Yasohara, Takasago (JP)

(73) Assignees: Kaneka Corporation, Osaka (JP); Ono Pharmaceutical Co., Ltd., Osaka (JP)

( * ) Notice: Subject to any disclaimer, the term of this patent is extended or adjusted under 35 U.S.C. 154(b) by 13 days.

(21) Appl. No.: 10/553,394

(22) PCT Filed: Apr. 16, 2004

(86) PCT No.: PCT/JP2004/005465

§ 371 (c)(1),
(2), (4) Date: Dec. 14, 2005

(87) PCT Pub. No.: WO2004/092113

PCT Pub. Date: Oct. 28, 2004

(65) Prior Publication Data

US 2006/0223152 A1    Oct. 5, 2006

(30) Foreign Application Priority Data

Apr. 18, 2003   (JP) ............................. 2003-114783

(51) Int. Cl.
*C07C 291/00*  (2006.01)
*C07C 237/16*  (2006.01)
*C07C 237/18*  (2006.01)
*C07C 237/20*  (2006.01)

(52) U.S. Cl. ...................... 562/553; 562/443; 560/115; 560/20

(58) Field of Classification Search ................. 562/553, 562/443, 521; 560/115, 20
See application file for complete search history.

(56) References Cited

U.S. PATENT DOCUMENTS 6,333,415 B1    12/2001    Yamamoto

FOREIGN PATENT DOCUMENTS

| JP | 58-26847 A | 2/1983 |
| JP | SHO-58-026847 | 2/1983 |
| JP | HEI-8-291106 | 11/1996 |
| WO | WO99/58513 | 11/1999 |

OTHER PUBLICATIONS

Bock et al., European Journal of Biochemistry (1971), 23(2), abstract.*

Ohtsuji, Kanazawa Daigaku Juzen Igakkai Zasshi (1996), 105(5), abstract.*

Suh et al., Chemical Communications (2002), 10, abstract.*

Baldwin et al., Biochemical Journal (1994), 301, abstract.*

Tsunoda et al., "Asymmetric induction in aza-claisen rearrangement of carboxamide enolates. Effect of chiral auxillary on nitrogen", Tetrahedron Letters, vol. 33, No. 12, pp. 1651-1654 (1992).*

Ito et al., "A few new methods for asymmetric synthesis", Pure & Applied chemistry, vol. 62, No. 7, p. 1405-1408 (1990).*

Ned A. Porter, et al, "Control of Dispersity and Stereo Chemistry in Free Radical Telomerizations: A Radical Addition, Cylization, Chain Transfer(ACT) Strategy", Journal of the American Chemical Society, vol. 116, No. 22, 1994, pp. 10255-10266 (compound 19a-d).

Stig Joensson, et al, "Enantiomers of Methyl-Substituted Analogs of (Z)-5-Decenyl Acetate as Probes for the Chirality and Complementarity of Its Receptor in *Agrotis segetum*: Synthesis and Structure-Activity Relationships", Journal of Chemical Ecology, vol. 19, No. 3 1993, pp. 459-484 (Fig. 2).

Mark J. Kurth, et al, "Asymmetric Induction in the Claisen Rearrangement of N-Allylketene N, O-Acetals", Journal of the American Chemical Society, vol. 107, No. 2, 1985, pp. 443-448 (compound 11r, 12s).

A.V. Rama Rao, et al, "Studies on Cyclo Depsipeptides-Part I: A Stereoselective Synthesis of C12 Polyketide Unit (C1-C8) Present in Jaspamide and Geodiamolide A-F", Tetrahedron Letters, vol. 34, No. 44, 1993, pp. 7081-7084 (compounds 7, 8).

Kunio Hiroi, et al, "Asymmetric Induction Reactions. II. Stereochemical Studies on Asymmetric [2, 3] Sigmatropic Rearrangements Using Chiral Ketenimines" Chemical & Pharmaceutical Bulletin, vol. 33, No. 11, 1985, pp. 4691-4700 (chart-2).

N. Porter, et al, Journal of the American Chemical Society, vol. 116, No. 22, 1994, pp. 10255-10266.

(Continued)

*Primary Examiner*—Cecilia Tsang
*Assistant Examiner*—Sun Jae Y Loewe
(74) *Attorney, Agent, or Firm*—Sughrue Mion, PLLC

(57) ABSTRACT

The present invention provides a process for producing an optically active 2-allylcarboxylic acid derivative, which is useful as a pharmaceutical intermediate, from readily available and inexpensive starting materials by the process which can be practiced on a commercial scale in a simple and easy manner, and certain 2-allylcarboxamide derivatives, which are novel and important intermediates in that process.

An N-allylcarboxamide derivative undergoes rearrangement reaction diastereoselectively in the presence of a base to give a 2-allylcarboxamide derivative, the resulting derivative is subjected to a carbamation reaction and solvolysis to give an optically active 2-allylcarboxylic acid ester, and then the ester obtained is stereoselectively hydrolyzed using an enzyme to produce 2-allylcarboxylic acid having a high optical purity. In addition, the present invention provides a 2-allylcarboxamide derivative compound which is a novel intermediate in the process of the present invention.

27 Claims, No Drawings

OTHER PUBLICATIONS

S. Jönsson, et al, Journal of Chemical Ecology, vol. 19, No. 3, 1993, pp. 459-484.

M. Kurth, et al, Journal of the American Chemical Society, vol. 107, No. 2, 1985, pp. 443-448.

A. Rao, et al, Tetrahedron Letters, vol. 34, No. 44, 1993, pp. 7081-7084.

K. Hirol, et al, Chemical & Pharmaceutical Bulletin, vol. 33, No. 11, 1985, pp. 4691-4700.

* cited by examiner

OPTICALLY ACTIVE 2-ALLYLCARBOXYLIC ACID DERIVATIVE AND PROCESS FOR PRODUCING THE SAME

TECHNICAL FIELD

The present invention relates to a novel intermediate compound, namely a 2-allylcarboxamide derivative, and to a process for producing an optically active 2-allylcarboxylic acid derivative utilizing such intermediate. For example, an optically active 2-allyloctanoic acid producible in accordance with the present invention is known to serve as an intermediate in the production of astrocyte function improvers (Japanese Kokai Publication Hei-07-316092).

BACKGROUND ART

Known in the art for the production of an optically active 2-allyloctanoic acid are 1) the process comprising reacting an octanamide compound of camphorsultam, which is an optically active compound, with diisopropyllithium amide, then reacting the product with an allyl halide to introduce an allyl group diastereoselectively into the octanamide moiety at the position 2 thereof, and eliminating the auxiliary camphorsultam group using a peracid or, alternatively, introducing a propargyl group in lieu of the above-mentioned allyl group, followed by reduction thereof to an allyl group (WO 99/58513), and 2) the process comprising optically resolving racemic propynyloctanoic acid by fractional crystallization using optically active phenethylamine and reducing the thus-obtained optical isomer (Japanese Kokai Publication Hei-08-291106), among others.

However, there are a number of problems in putting the above-mentioned process (1) into practice on a commercial scale; for example, camphorsultam, which is a very expensive chiral auxiliary group, is required, the allylation or propalgylation reaction is to be carried out at a very low temperature of −78° C., and hydrogen peroxide is required to eliminate the auxiliary camphorsultam group. As for the prior art process (2), the optical resolution efficiency is low and, for obtaining 2-propynyloctanoic acid having a sufficiently high optical purity for use as an pharmaceutical intermediate, in particular, a plurality of repetitions of fractional crystallization are required, which inevitably results in a reduction in yield.

SUMMARY OF THE INVENTION

In view of the above-discussed problems with the prior art processes, the present inventors made intensive investigations in an attempt to develop a process capable of being carried out safely even on a large scale using only those starting materials or reagents which can be handled with ease on an industrial scale and are inexpensive and readily available. As a result, they have developed a process for producing and obtaining 2-allylcarboxylic acids having a high optical purity with great efficiency via novel and important intermediates, namely 2-allylcarboxamide compounds by utilizing very inexpensive optically active sources as asymmetric auxiliary groups, stereoselectively allylating carboxylic acids at the position 2 thereof without utilizing any very low temperature reaction, realizing protective group elimination very efficiently and, further, utilizing an enzymatic reaction.

Thus, the present invention provides a process for producing an optically active 2-allylcarboxylic acid represented by the following formula (5);

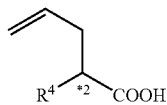

wherein $R^4$ represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms and *2 indicates that the carbon atom marked therewith is an asymmetric carbon atom;, which comprises:

(a) reacting a carboxamide compound represented by the following formula (2);

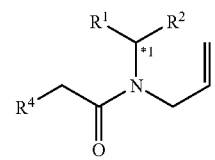

wherein $R^1$, $R^2$ and $R^4$ each independently represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms and *1 indicates that the carbon atom marked therewith is an asymmetric carbon atom;

with an organometallic compound and then further with a compound represented by the formula;

ClCOOR⁵ wherein $R^5$ represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms; to give a 2-allylcarboxamide derivative represented by the following formula (3);

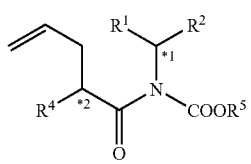

wherein $R^1$, $R^2$, $R^4$, $R^5$, *1 and *2 are as defined above;

(b) reacting the derivative (3) with a compound represented by the formula MOR⁶ wherein M represents an alkali metal and $R^6$ represents a substituted or unsubstituted alkyl group containing 1 to 20 carbon atoms to give a 2-allylcarboxylic acid ester derivative represented by the following formula (4);

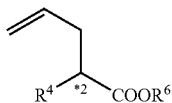

(4)

wherein $R^4$, $R^6$ and *2 are as defined above; and
(c) further hydrolyzing the derivative (4).

The invention also provides
a process for producing a 2-allylcarboxamide derivative represented by the following formula (6);

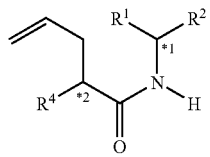

(6)

wherein $R^1$, $R^2$, $R^4$ and *1 are as defined above and *2 indicates that the carbon atom marked therewith is an asymmetric carbon atom;
which comprises reacting a carboxamide compound represented by the formula (2) given above with an organometallic compound.

The invention also provides
a process for producing a 2-allylcarboxamide derivative represented by the formula (3) given above,
which comprises reacting a compound represented by the formula (6) given above in the presence of a base and further with a compound represented by the formula;

ClCOOR$^5$ wherein $R^5$ is as defined above.

The invention further provides
a process for producing a 2-allylcarboxamide derivative represented by the formula (3) given above,
which comprises reacting a carboxamide compound represented by the formula (2) given above with an organometallic compound and further with a compound represented by the formula;

ClCOOR$^5$ wherein $R^5$ is as defined above.

The invention further provides
a process for producing a 2-allylcarboxylic acid represented by the following formula (8);

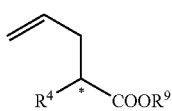

(8)

wherein $R^4$ is as defined hereinabove, $R^9$ represents a hydrogen atom or a substituted or unsubstituted alkyl group containing 1 to 20 carbon atoms, and * indicates that the carbon atom marked therewith is an asymmetric carbon atom or an ester derivative thereof;
which comprises reacting a 2-allylcarboxamide derivative represented by the following formula (7);

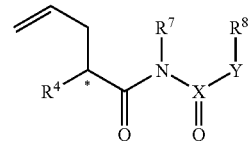

(7)

wherein $R^4$ is as defined hereinabove, $R^7$ and $R^8$ each represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms and $R^7$ and $R^8$ may be bound together to form a ring, X represents C, S or S(O), Y represents CH, O or NH and * is as defined hereinabove;

with a compound represented by the formula MOR$^9$ wherein M represents an alkali metal and $R^9$ is as defined hereinabove and,
if necessary, hydrolyzing the resulting ester.

The invention still further provides
a process for producing an optically active 2-allylcarboxylic acid represented by the formula (5) given above,
which comprises causing an enzyme source having asymmetric hydrolysis activity to act on a 2-allylcarboxylic acid ester derivative represented by the formula (4) given above and
collecting the resulting optically active 2-allylcarboxylic acid.

Furthermore, the invention provides
a process for producing an optically active 2-allylcarboxylic acid ester represented by the formula (4) given above,
which comprises causing an enzyme source having asymmetric hydrolysis activity to act on a 2-allylcarboxylic acid ester derivative represented by the formula (4) given above and
collecting the unreacted optically active 2-allylcarboxylic acid ester.

Finally, the invention relates to
a 2-allylcarboxamide derivative compound represented by the following formula (1);

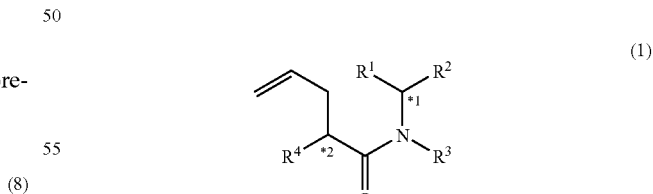

(1)

wherein $R^1$, $R^2$, $R^3$, $R^4$, *1 and *2 are as defined above.

DETAILED DESCRIPTION OF THE INVENTION

In the following, the invention is described in detail.
First, the 2-allylcarboxamide derivative compound represented by the formula (1) is described.

In the formula, $R^1$ and $R^2$ each independently represents an alkyl group, aryl group or aralkyl group. The alkyl group is a substituted or unsubstituted one containing 1 to 18 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, isopentyl group or n-hexyl group.

The aryl group is a substituted or unsubstituted one containing 6 to 20 (preferably 6 to 10) carbon atoms, such as, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group or 4-bromophenyl group.

The aralkyl group is a substituted or unsubstituted one containing 7 to 20 (preferably 7 to 10) carbon atoms, such as, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group or 2-phenylpropyl group.

Preferred as $R^1$ is a substituted or unsubstituted aryl group containing 6 to 20 carbon atoms. In particular, phenyl group, 4-methylphenyl group, 4-methoxyphenyl group, 3-methoxyphenyl group, 4-nitrophenyl group, 4-chlorophenyl group, 4-bromophenyl group, 1-naphthyl group and 2-naphthyl group are preferred. Preferred as $R^2$ is a substituted or unsubstituted alkyl group containing 1 to 18 carbon atoms and, in particular, methyl group is preferred.

The combination of $R^1$ and $R^2$ may be that of any two substituents arbitrarily selected from among those specifically enumerated hereinabove. Preferred are the combination of an aryl group as $R^1$ and an alkyl group as $R^2$ and the combination of an aryl group as $R^1$ and an aralkyl group as $R^2$. More preferred are the combination of phenyl group, 4-methylphenyl group, 1-naphthyl group, 2-naphthyl group, 4-methoxyphenyl group, 3-methoxyphenyl group, 4-nitrophenyl group, 4-chlorophenyl group or 4-bromophenyl group as $R^1$ and methyl group as $R^2$ and the combination of phenyl group as $R^1$ and 4-methylbenzyl group as $R^2$. More preferred is the combination of phenyl group as $R^1$ and methyl group as $R^2$.

In the relevant formula, $R^4$ represents an alkyl group, aryl group or aralkyl group. The alkyl group is a substituted or unsubstituted one containing 1 to 18 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, isopentyl group or n-hexyl group.

The aryl group is a substituted or unsubstituted one containing 6 to 20 (preferably 6 to 10) carbon atoms, such as, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group or 4-bromophenyl group.

The aralkyl group is a substituted or unsubstituted one containing 7 to 20 (preferably 7 to 10) carbon atoms, such as, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group or 2-phenylpropyl group.

Among those groups, an alkyl group is preferred as $R^4$, and n-hexyl group is more preferred.

$R^3$ represents a hydrogen atom, an alkyloxycarbonyl group, an aryloxycarbonyl group or an aralkyloxycarbonyl group.

The alkyloxycarbonyl group is a substituted or unsubstituted one containing 2 to 20 (preferably 2 to 11, more preferably 2 to 7) carbon atoms, such as, for example, methyloxycarbonyl group, ethyloxycarbonyl group, n-propyloxycarbonyl group, isopropyloxycarbonyl group, n-butyloxycarbonyl group, isobutyloxycarbonyl group, sec-butyloxycarbonyl group, tert-butyloxycarbonyl group, n-pentyloxycarbonyl group, isopentyloxycarbonyl group or n-hexyloxycarbonyl group.

The aryloxycarbonyl group is a substituted or unsubstituted one containing 7 to 20 (preferably 7 to 11) carbon atoms, such as, for example, phenyloxycarbonyl group, 1-naphthyloxycarbonyl group, 2-naphthyloxycarbonyl group, 4-methylphenyloxycarbonyl group, 3-methylphenyloxycarbonyl group, 2-methylphenyloxycarbonyl group, 4-ethylphenyloxycarbonyl group, 3-ethylphenyloxycarbonyl group, 4-methoxyphenyloxycarbonyl group, 3-methoxyphenyloxycarbonyl group, 2-methoxyphenyloxycarbonyl group, 4-nitrophenyloxycarbonyl group, 4-phenylphenyloxycarbonyl group, 4-chlorophenyloxycarbonyl group or 4-bromophenyloxycarbonyl group.

The aralkyloxycarbonyl groups is a substituted or unsubstituted one containing 8 to 20 (preferably 8 to 11) carbon atoms, such as, for example, benzyloxycarbonyl group, 4-methylbenzyloxycarbonyl group, 3-methylbenzyloxycarbonyl group, 2-methylbenzyloxycarbonyl group, 4-methoxybenzyloxycarbonyl group, 3-methoxybenzyloxycarbonyl group, 2-methoxybenzyloxycarbonyl group, 3-phenylpropyloxycarbonyl group or 2-phenylpropyloxycarbonyl group.

As preferred species, there may be mentioned a hydrogen atom, phenyloxycarbonyl group, isopropyloxycarbonyl group, isobutyloxycarbonyl group, sec-butyloxycarbonyl group and tert-butyloxycarbonyl group. More preferred are a hydrogen atom, phenyloxycarbonyl group and isopropyloxycarbonyl group.

The asymmetric carbon atom marked with *1 may have either the R-form absolute configuration or the S-form absolute configuration. Similarly, the asymmetric carbon atom marked with *2 may have either the R-form absolute configuration or the S-form absolute configuration.

Now, the step of producing the 2-allylcarboxamide derivative of the formula (3) by reacting the carboxamide compound of the formula (2) with an organometallic compound and then with a chlorocarbonate ester of the formula $ClCOOR^5$ is described.

The compound (2) to be used in this step can be prepared, for example by the amidation reaction between the corresponding carboxylic acid halide or carboxylic anhydride and N-allylamine derivative, which are readily available, or by the N-allylation reaction of the corresponding carboxamide compound. The compound (2) to be used may be in the form of a racemic mixture or in an optically active form. The use of an optically active form is preferred.

In the relevant formulas, $R^1$ and $R^2$ each independently represents an alkyl group, aryl group or aralkyl group. The alkyl group is a substituted or unsubstituted one containing 1 to 18 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, isopentyl group or n-hexyl group.

The aryl group is a substituted or unsubstituted one containing 6 to 20 (preferably 6 to 10) carbon atoms, such as, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group or 4-bromophenyl group.

The aralkyl group is a substituted or unsubstituted one containing 7 to 20 (preferably 7 to 10) carbon atoms, such as, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group or 2-phenylpropyl group.

Preferred as $R^1$ in the formula (2) is an aryl group and, in particular, phenyl group, 4-methylphenyl group, 4-methoxyphenyl group, 3-methoxyphenyl group, 4-nitrophenyl group, 4-chlorophenyl group, 4-bromophenyl group, 1-naphthyl group and 2-naphthyl group are preferred.

Preferred as $R^2$ in the formula (2) are methyl group, benzyl group and 4-methylbenzyl group, and methyl group and 4-methylbenzyl group are more preferred.

The combination of $R^1$ and $R^2$ may be that of any two substituents arbitrarily selected from among those specifically enumerated hereinabove. Preferred are the combination of an aryl group as $R^1$ and an alkyl group as $R^2$ and the combination of an aryl group as $R^1$ and an aralkyl group as $R^2$. More preferred are the combination of phenyl group, 4-methylphenyl group, 1-naphthyl group, 2-naphthyl group, 4-methoxyphenyl group, 3-methoxyphenyl group, 4-nitrophenyl group, 4-chlorophenyl group or 4-bromophenyl group as $R^1$ and methyl group as $R^2$ and the combination of phenyl group as $R^1$ and 4-methylbenzyl group as $R^2$. More preferred is the combination of phenyl group as $R^1$ and methyl group as $R^2$.

In the relevant formulas, $R^4$ represents an alkyl group, aryl group or aralkyl group. The alkyl group is a substituted or unsubstituted one containing 1 to 18 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, isopentyl group or n-hexyl group.

The aryl group is a substituted or unsubstituted one containing 6 to 20 (preferably 6 to 10) carbon atoms, such as, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group or 4-bromophenyl group.

The aralkyl group is a substituted or unsubstituted one containing 7 to 20 (preferably 7 to 10) carbon atoms, such as, for example, benzyl group, 4-methylbenzyl group, 3-methylbenzyl group, 2-methylbenzyl group, 4-methoxybenzyl group, 3-methoxybenzyl group, 2-methoxybenzyl group, 2-phenylethyl group, 1-(4-methylphenyl)ethyl group, 1-(4-methoxyphenyl)ethyl group, 3-phenylpropyl group or 2-phenylpropyl group.

Among those, an alkyl group is preferred, and n-hexyl is more preferred.

The organometallic compound to be used includes organolithium compounds, organopotassium compounds and organomagnesium compounds. Organomagnesium compounds are preferred, tert-butylmagnesium halides are more preferred, and tert-butylmagnesium chloride is most preferred. As for the usage, the organometallic compound is to be used generally in an amount of not less than 1 mole, preferably 1.0 to 2.0 moles, more preferably 1.1 to 1.3 moles, per mole of the compound of the formula (2).

In the formula $ClCOOR^5$, $R^5$ represents an alkyl group, aryl group or aralkyl group.

The alkyl group is a substituted or unsubstituted one containing 1 to 18 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, isopentyl group or n-hexyl group.

The aryl group is a substituted or unsubstituted one containing 6 to 20 (preferably 6 to 10) carbon atoms, such as, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group or 4-bromophenyl group.

The aralkyl group is a substituted or unsubstituted one containing 7 to 20 (preferably 7 to 10) carbon atoms, such as, for example, benzyl group, 4-methylbenzyl group, 3-methylbenzyl group, 2-methylbenzyl group, 4-methoxybenzyl group, 3-methoxybenzyl group, 2-methoxybenzyl group, 3-phenylpropyl group or 2-phenylpropyl group.

Preferred as $R^5$ are phenyl group, isopropyl group, isobutyl group, sec-butyl group and tert-butyl group. More preferred are phenyl group and isopropyl group.

The usage of the chlorocarbonate compound represented by the formula $ClCOOR^5$ is not particularly restricted but should be not less than 1 mole per mole of the compound (2). Preferably, it is 1.0 to 5.0 moles per mole of the compound (2).

The solvent to be used in carrying out the reaction is not particularly restricted but may be any of those which will not adversely affect the reaction. Thus, there maybe mentioned, for example, hexane, toluene, xylene, tetrahydrofuran, diethyl ether, tert-butylmethyl ether, ethylene glycol dimethyl ether, ethylene glycol diethyl ether, dimethylformamide (DMF), and mixtures of these. Toluene is preferred.

As for the reaction temperature, the reaction with the organometallic compound is generally carried out at 25° C. to 100° C., preferably 60° C. to 90° C. The reaction time, which may vary depending on the reaction temperature and the amount of the organometallic compound used, is generally 1 hour to 24 hours, preferably 5 hours to 10 hours.

The reaction with the chlorocarbonate $ClCOOR^5$ is generally carried out at 0° C. to 100° C., preferably 10° C. to 70° C., more preferably 20° C. to 50° C. The reaction time, which may vary depending on the usage of $ClCOOR^5$ and the reaction temperature, is generally 1 hour to 48 hours, preferably 5 hours to 24 hours.

The process for producing the compound (3) from the compound (2) can be carried out continuously, as mentioned above. If necessary, however, the reactions may be carried out each independently. Thus, it is possible to derive the compound of the formula (6) from the compound of the formula (2) by reaction with the organometallic compound, then react the compound (6) in the presence of a base and further with the compound $ClCOOR^5$ to produce the compound (3). $R^1$, $R^2$, $R^4$ and $R^5$ are as described hereinabove.

The mode of practice of the step of producing the compound (6) from the compound (2) is as described above. The mode of practice of the step of deriving the compound (3) from the compound (6) is also as described above, wherein the base is an alkali metal compound or an alkaline earth metal compound. As the alkali metal compound, there may be mentioned organolithium compounds, organopotassium compounds and, further, alkali metal hydrides. Among those, alkali metal hydrides, such as sodium hydride, potassium hydride and lithium hydride, are preferred, and sodium hydride is more preferred. As the alkaline earth metal compound, there may be mentioned such organomagnesium compounds as mentioned hereinabove.

After the reaction, the compound (3) or compound (6) formed can be recovered by extraction with an organic solvent such as ethyl acetate, ether, hexane or toluene and, if necessary, can be purified and isolated by such a procedure as chromatography, crystallization or distillation. The compound (3) or compound (6) is generally formed as a diastereomer mixture. However, the diastereomeric excess can be appropriately increased by crystallization. Here, the diastereomeric excess is defined as follows:

[(amount of diastereomer A− amount of diastereomer B)/(amount of diastereomer A+ amount of diastereomer B)]×100.

The solvent to be used in crystallization is not particularly restricted but includes, among others, pentane, hexane, heptane, octane, water, methanol, ethanol, n-propanol, isopropanol, n-butanol, isobutanol, tert-butanol, benzene, xylene, trimethylbenzene, tetrahydrofuran, tetrahydropyran, 1,3-dioxane, 1,4-dioxane, methyl acetate, ethyl acetate, n-propyl acetate, isopropyl acetate, n-butyl acetate, isobutyl acetate, tert-butyl acetate, dimethyl ether, tert-butyl methyl ether, acetonitrile, propionitrile, butyronitrile, acetone, DMF, dimethyl sulfoxide (DMSO), N-methylpyrrolidone (NMP), and mixed solvents comprising two or more of these. The crystallization condition can be properly determined.

The reaction product can be used in the next step without extraction, if necessary after dehydration or dehydration and concentration.

The step of producing the compound (4) from the compound (3) is now described. In this step, the compound (4) is produced by reacting the compound (3) with a compound represented by the formula $MOR^6$. $R^1$, $R^2$, $R^4$ and $R^5$ are as described hereinabove.

As $R^6$ in the formula $MOR^6$, there may be mentioned a substituted or unsubstituted alkyl group containing 1 to 20 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, sec-pentyl group and isopentyl group. Methyl group and ethyl group are preferred, and methyl group is more preferred.

M represents an alkali metal atom such as a lithium atom, sodium atom and potassium atom. A sodium atom is preferred.

As for the usage of the compound represented by the formula $MOR^6$, that compound is generally used in an amount of not less than 1 mole, preferably 1.1 to 3.0 moles, per mole of the compound (3). When used in combination in an amount of not less than 1.0 mole per mole of the compound (3), however, the amount of $MOR^6$ may be 1.0 mole or less per mole of the compound (3). When $R^6OH$ is used, the amount thereof is not less than 1.0 mole per mole of the compound (3), without any further particular restriction. Furthermore, in that case, the amount of $MOR^6$ is preferably 0.01 to 10.0 moles, more preferably 0.1 to 3.0 moles, still more preferably 0.5 to 2.5 moles, per mole of the compound (3).

The solvent to be used is not particularly restricted but may be any of those which will not adversely affect the reaction. Thus, there may be mentioned, in addition to the above-mentioned $R^6OH$, hexane, toluene, xylene, tetrahydrofuran, diethyl ether, tert-butyl methyl ether, DMF, DMSO, NMP, and mixtures of these. Among them, hexane and tetrahydrofuran are particularly preferred.

The reaction is generally carried out at −20° C. to 50° C., preferably −10° C. to 30° C. The reaction time is generally 0.5 hour to 24 hours, preferably 1 hour to 18 hours.

After the reaction, the compound (4) formed can be recovered by extraction with an organic solvent such as ethyl acetate, toluene, hexane or ether and, if necessary, can be purified by such a procedure as chromatography, crystallization or distillation. The reaction mixture may be used in the next step without extraction, if necessary after dehydration or dehydration and concentration.

The step of deriving the compound (8) from the compound (7) is now described. $R^4$ is as described hereinabove. In the relevant formula, $R^7$ and $R^8$ each represents an alkyl group containing 1 to 18 carbon atoms, an aryl group containing 6 to 20 carbon atoms or an aralkyl group containing 7 to 20 carbon atoms and they maybe bound together to form a ring. Furthermore, an asymmetric carbon atom may be contained therein.

The alkyl group is a substituted or unsubstituted one containing 1 to 18 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, isopentyl group or n-hexyl group.

The aryl group is a substituted or unsubstituted one containing 6 to 20 (preferably 6 to 10) carbon atoms, such as, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group or 4-bromophenyl group.

The aralkyl group is a substituted or unsubstituted one containing 7 to 20 (preferably 7 to 10) carbon atoms, such as, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 3-phenylpropyl group or 2-phenylpropyl group.

In cases where $R^7$ and $R^8$ are bound together, the compound of the formula (7) is represented by the following formula (9);

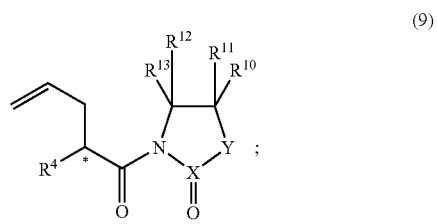

(9)

or the following formula (10);

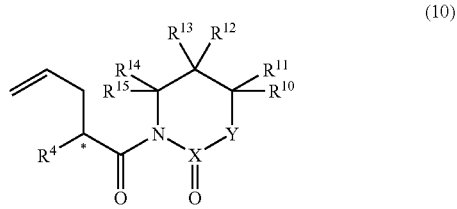

(10)

wherein $R^4$, X, Y and * are as defined hereinabove and $R^{10}$, $R^{11}$, $R^{12}$, $R^{13}$, $R^{14}$ and $R^{15}$ each independently represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms.

Preferred as $R^7$ is 1-phenylethyl group having the (R) or (S) absolute configuration. Preferred as $R^8$ are phenyl group and isopropyl group.

In the formulas (7), (9) and (10), X represents C, S or S(O), and Y represents CH, O or NH. Carbon is preferred as X, and oxygen is preferred as Y.

As $R^9$ in the formula $MOR^9$, there may be mentioned a hydrogen atom or a substituted or unsubstituted alkyl group containing 1 to 20 (preferably 1 to 10, more preferably 1 to 6) carbon atoms, such as, for example, methyl group, ethyl group, n-propyl group, isopropyl group, n-butyl group, isobutyl group, sec-butyl group, tert-butyl group, n-pentyl group, sec-pentyl group and isopentyl group. Among them, methyl group and ethyl group are preferred, and methyl group is more preferred.

M represents an alkali metal atom, such as a lithium atom, sodium atom or potassium atom. A sodium atom is preferred.

As for the usage, the compound represented by the formula $MOR^9$ is generally used in an amount of not less than 1 mole, preferably 1.1 to 3.0 moles, per mole of the compound (7). When $R^9OH$ (wherein $R^9$ is other than H) is used in combination in an amount of not less than 1.0 mole per mole of the compound (7), however, the amount of $MOR^9$ may be 1.0 mole or less per mole of the compound (7). When $R^9OH$ is used, the amount thereof is not less than 1.0 mole, without any further particular restriction. Furthermore, in that case, the amount of $MOR^9$ is preferably 0.01 to 10.0 moles, more preferably 0.1 to 3.0 moles, still more preferably 0.5 to 2.5 moles, per mole of the compound (7).

When $R^9$ in $MOR^9$ is a hydrogen atom, it is generally possible to carry out the reaction in the presence of hydrogen peroxide according to need and, in this case, the compound (8) formed is a 2-allylcarboxylic acid represented by the formula (5) given hereinabove. When $R^9$ is other than a hydrogen atom, the compound (8) formed is a 2-allylcarboxylic acid ester represented by the formula (4) given hereinabove. When the product is a 2-allylcarboxylic acid ester (4), this may be converted to the corresponding 2-allylcarboxylic acid (5) by hydrolysis according to need. When hydrogen peroxide is used, this is used generally in an amount of not less than 1.0 mole, preferably 1.0 to 50 moles, more preferably 1.1 to 30 moles, per mole of $MOR^9$.

The solvent to be used is not particularly restricted but may be any of those which will not adversely affect the invention. Thus, there may be mentioned, in addition to above mentioned $R^9OH$, hexane, toluene, xylene, tetrahydrofuran, diethyl ether, tert-butyl methyl ether, DMF, DMSO, NMP, and mixed solvents composed of two or more of these. Preferred are hexane and tetrahydrofuran, in particular.

The reaction is generally carried out at −20° C. to 50° C., preferably −10° C. to 30° C. The reaction time is generally 0.5 hour to 24 hours, preferably 1 hour to 18 hours.

After the reaction, the compound (8) formed can be recovered by extraction with an organic solvent such as ethyl acetate, toluene, hexane or ether and, if necessary, can be purified by such a procedure as chromatography, crystallization or distillation. The reaction mixture may be used in the next step without extraction, if necessary after dehydration or dehydration and concentration.

Finally, the step of producing the compound (5) from the compound (4) is described. $R^4$ and $R^6$ are as described hereinabove. In this step, any of those methods generally used in hydrolyzing esters can be employed without any particular restriction. More preferably, however, the compound (4) is stereoselectively hydrolyzed using an enzyme source capable of asymmetrically hydrolyzing the same to give a product improved in optical purity. The compound (4) to be used may be either a racemic mixture or an optically active form.

The enzyme source is not particularly restricted but may be any one capable of stereoselectively hydrolyzing the ester moiety of the compound (4). The enzyme may be a microorganism-derived, animal cell-derived or plant cell-derived one. Specifically, there may be mentioned enzyme sources derived from microorganisms belonging to the genus *Candida, Humicola, Mucor, Pseudomonas, Rhizopus, Brevundimonas, Cellulomonas, Jensenia, Rhodococcus, Saccharomycopsis* or *Trichosporon*.

More specifically, mention may be made of enzyme sources derived from *Candida antarctica, Candida lipolitica, Candida cylindracea, Candida rugosa, Humicola* sp., *Humicola lanuginosa, Mucor meihei, Mucor javanicus, Pseudomonas* sp., *Rhizopus delemar, Rhizopus javanicus, Brevundimonas diminuta, Cellulomonas fimi, Jensenia canicruria, Rhodococcus erythropolis, Candida pini, Saccharomycopsis selenospora, Trichosporon cutaneum* or *Trichosporon debeurmannianum*.

The "enzyme source" so referred to herein includes not only purified enzymes but also roughly purified enzymes and microbial cells, and the like. Furthermore, the enzyme or microbial cells may be immobilized on an inorganic carrier, organic polymer carrier, and/or the like.

The hydrolysis reaction using the enzyme source mentioned above may be carried out in water or in a mixed solvent composed of water and an organic solvent. The organic solvent to be used in admixture with water is, for example, methanol, ethanol, propanol, acetone, dioxane, tetrahydrofuran, toluene or ethyl acetate. The substrate compound (4) or compound (8) is used in an amount within the range of 0.1 to 50% by weight on the reaction mixture basis, and the enzyme source is used in an amount of 0.01 to 500% byweight based on the substrate, although the amount thereof may depend on the mode of utilization thereof. The enzyme source may be added either all at once at the start of the reaction or in divided portions. Similarly, the substrate compound (4) or compound (8) may be added either all at once at the start of the reaction or in divided portions.

The temperature at which the enzyme source is to act on the substrate is preferably 10 to 60° C., more preferably 25 to 40° C., and may depend on the properties of the enzyme.

The pH of the reaction mixture is preferably within the range of 3 to 10, more preferably within the range of 5 to 8. For the pH adjustment of the solution, an aqueous solution of an alkali such as sodium hydroxide or sodium carbonate may be used or, alternatively, a buffer solution such as a phosphate buffer may be used. The pH value may be decreased with the progress of the reaction in some instances. As long as the pH value is within the above-mentioned preferred range, no pH adjustment will be required. Optionally, the pH value may be maintained at a constant level by adequate addition of an aqueous solution of an alkali.

After completion of the reaction, the unreacted optically active compound (4) or compound (8) maybe isolated by adjusting the reaction mixture to an alkaline pH by addition thereto of an aqueous solution of an alkali such as sodium hydroxide and extracting the organic phase with an organic solvent such as ethyl acetate, hexane or toluene. After extraction with the organic phase, the aqueous phase is adjusted to an acidic pH by addition thereto of an acid such as sulfuric acid and extracted with such an organic solvent as ethyl acetate, hexane or toluene, where-upon the optically active compound (5), which is the hydrolysis product, can be isolated. Furthermore, each compound can be purified by distillation, silica gel column chromatography, and the like.

of toluene was cooled to 0° C., and 73.85 g (453.9 mmol) of octanoyl chloride was added dropwise thereto. After completion of the addition, the reaction was allowed to proceed at room temperature for 3 hours. The reaction mixture was again cooled to 0° C. and then the reaction was terminated by addition of 200 ml of 10% hydrochloric acid. The toluene phase was separated, washed with 300 ml of a 10% aqueous solution of sodium hydroxide, and dried over anhydrous sodium sulfate. The solvent was then distilled off, and the residue was quantitated by HPLC. Thus was obtained 19.81 g (97%) of the title compound.

$^1$H-NMR (400 MHz, $CDCl_3$) δ 0.87 (t, 3H, J=7.3 Hz), 1.26-1.29 (m, 8H), 1.48 (d, 3H, J=7.1 Hz), 1.61-1.64 (m, 2H), 2.17 (t, 2H, J=7.3 Hz), 5.15 (q, 1H, J=7.1 Hz), 5.64 (brs, 1H), 7.28-7.36 (m, 5H).

PREPARATION EXAMPLES 2 to 5

The compounds given in Table 1 were obtained in the same manner as in Preparation Example 1.

TABLE 1

| Preparation Example | Compound | Yield (%) | $^1$H-NMR (400 Mz, $CDCl_3$) |
|---|---|---|---|
| 2 | n-C$_7$H$_{15}$-C(O)-NH-CH(CH$_3$)-C$_6$H$_4$-OMe (para) | 95 | 0.87 (t, 3 H, J = 7.3 Hz), 1.26-1.30 (m, 8 H), 1.46 (d, 3 H, J = 6.8 Hz), 1.61 (t, 2 H, J = 7.1 Hz), 2.15 (q, 2 H, J = 7.3 Hz), 3.79 (s, 3 H), 5.09 (q, 1 H, J = 6.8 Hz), 5.70 (brs, 1 H), 6.85-6.88 (m, 2 H) 7.22-4.26 (m, 2 H). |
| 3 | n-C$_7$H$_{15}$-C(O)-NH-CH(CH$_3$)-C$_6$H$_4$-OMe (meta) | 96 | 0.86 (t, 3 H, J = 7.3 Hz), 1.28-1.30 (m, 8 H), 1.46 (d, 3 H, J = 7.1 Hz), 1.59-1.70 (m, 2 H), 2.17-2.32 (m, 2 H), 3.79 (s, 3 H), 5.08 (m, 1 H), 5.82-5.77 (m, 1 H), 6.73-6.89 (m, 3 H), 7.21-7.29 (m, 1 H). |
| 4 | n-C$_7$H$_{15}$-C(O)-NH-CH(CH$_3$)-(1-naphthyl) | 98 | 0.86 (t, 3 H, J = 7.3 Hz), 1.23-1.26 (m, 8 H), 1.60-1.63 (m, 2 H), 1.67 (d, 2 H, J = 6.6 Hz), 2.12-2.17 (m, 2 H), 5.62 (brs, 1 H), 5.95 (q, 1 H, J = 6.6 Hz), 7.44-7.56 (m. 4H), 7.79-7.88 (m, 2 H), 8.09 (d, 1 H, J = 8.1 Hz). |
| 5 | n-C$_7$H$_{15}$-C(O)-NH-CH(Ph)-CH$_2$-C$_6$H$_4$-CH$_3$ | 96 | 0.87 (t, 3 H, J = 7.3 Hz), 1.23-1.29 (m, 8 H), 1.51-1.57 (m, 2 H), 2.11 (t, 2 H, J = 7.3 Hz), 2.29 (s, 3 H), 3.00-3.12 (m, 2 H), 5.27 (q, 1 H, J = 7.3 Hz), 5.65 (brs, 1 H), 6.94 (d, 2 H, J = 8.1 Hz), 7.03 (d, 2 H, J = 8.1 Hz), 7.26-7.32 (m, 5 H). |

BEST MODES FOR CARRYING OUT THE INVENTION

The following examples illustrate the present invention in further detail. These are, however, by no means limitative of the scope of the invention.

PREPARATION EXAMPLE 1

(R)-N-Octanoyl-1-phenylethylamine

A solution of 50.0 g (412.6 mmol) of (R)-1-phenylethylamine and 41.75 g (412.6 mmol) of triethylamine in 750 ml

PREPARATION EXAMPLE 6

(R)-N-Octanoyl-1-phenylethylamine

Octanoic anhydride (5.58 g, 20.6 mmol) was added dropwise to a solution of 2.75 g (22.7 mmol) of (R)-1-phenylethylamine and 2.09 g (20.6 mmol) of triethylamine in 35 ml of toluene at room temperature. The reaction was allowed to proceed for 18 hours and then the reaction was terminated by addition of 20 ml of 10% hydrochloric acid. The toluene phase was separated, washed with two 30-ml portions of 10% sodium hydroxide and dried over anhydrous sodium sulfate. After removal of the solvent by distillation, the residue was quantitated by HPLC. Thus was obtained 4.55 g (89%) of the title compound.

PREPARATION EXAMPLE 7

(R)-N-Allyl-N-octanoyl-1-phenylethylamine

Sodium hydride (60%) (0.65 g, 16.3 mmol) was washed with three 20-ml portions of hexane and then suspended in 5 ml of THF. Hereto were added a solution of 2.00 g (8.1 mmol) of (R)-N-octanoyl-1-phenylethylamine in 15 ml of THF, and 1.96 g (16.3 mmol) of allyl bromide, and the reaction was allowed to proceed at room temperature for 1 hour and, then, at 70° C. for 2 hours. The reaction mixture was cooled to room temperature and added dropwise to 20 ml of ice-cooled 1 M hydrochloric acid to thereby terminate the reaction. The resulting mixture was extracted with 30 ml of hexane. The organic phase was washed with a saturated aqueous solution of sodium chloride and dried over anhydrous sodium sulfate, and the solvent was then distilled off. The desired product was purified on a silica gel column. Thus was obtained 7.59 g (94%) of the title compound.

$^1$H-NMR (400 MHz, CDCl$_3$) δ 0.87 (t, 3H, J=7.3 Hz), 1.28-1.30 (m, 8H), 1.48 (d, 3H, J=7.1 Hz), 1.61-1.68 (m, 2H), 2.81 (t, 2H, J=7.3 Hz), 3.58-3.74 (m, 2H), 4.96-5.08 (m, 2H), 5.55-5.62 (m, 1H), 6.12 (q, 1H, J=7.1 Hz), 7.23-7.36 (m, 5H).

PREPARATION EXAMPLES 8 TO 11

The compounds given in Table 2 were obtained in the same manner as in Preparation Example 7.

PREPARATION EXAMPLE 12

(R)-N-Allyl-N-octanoyl-1-phenylethylamine

A solution of 10.0 g (40.0 mmol) of (R)-N-octanoyl-1-phenylethylamine in 20 ml of toluene, and 9.90 g (80.0 mmol) of allyl bromide were added to a suspension of 3.20 g (80.0 mmol) of sodium hydride (60%) in 74 ml of toluene, and the reaction was allowed to proceed at 100° C. for 6 hours. The reaction mixture was cooled to room temperature and added dropwise to 80 ml of ice-cooled 1 N hydrochloric acid to thereby terminate the reaction. The resulting mixture was extracted with three 30-ml portions of hexane. The organic phase was washed with 50 ml of water and then dried over anhydrous sodium sulfate, and the solvent was distilled off. The residue was quantitated by HPLC. Thus was obtained 9.87 g (86%) of the title compound.

EXAMPLE 1

(R)-N-(2-Allyloctanoyl)-1-phenylethylamine

To a solution of 24.0 g (83.0 mmol) of (R)-N-allyl-N-octanoyl-1-phenylethylamine in 240 ml of toluene was added dropwise 61.5 ml (98.0 mmol) of tert-butylmagnesium chloride (1.6 M) at room temperature and, after completion of the addition, the reaction was allowed to

TABLE 2

| Preparation Example | Compound | Yield (%) | $^1$H-NMR (400 Mz, CDCl$_3$) |
|---|---|---|---|
| 8 | n-C$_7$H$_{15}$-C(=O)-N(allyl)-CH(CH$_3$)-C$_6$H$_4$-OMe (para) | 99 | 0.86-0.89 (m, 3 H), 1.28-1.30 (m, 8 H), 1.45 (d, 2 H, J = 7.3 Hz), 1.57-1.69 (m, 3 H), 2.17-2.47 (m, 2H), 3.37-4.08 (m, 5 H), 4.96-5.13 (m, 2 H), 5.52-6.10 (m, 2 H), 6.84-6.89 (m, 2 H), 7.21-7.27 (m, 2 H). |
| 9 | n-C$_7$H$_{15}$-C(=O)-N(allyl)-CH(CH$_3$)-C$_6$H$_4$-OMe (meta) | 96 | 0.84-0.87 (m, 3 H), 1.25-1.28 (m, 8 H), 1.47 (d, 2 H, J = 6.8 Hz), 1.61-1.64 (m, 3 H), 2.31-2.35 (m, 2 H), 3.61-3.67 (m, 1 H), 3.70-3.80 (m, 4 H), 5.07-5.14 (m, 2 H), 5.50-5.69 (m, 1 H), 6.06-6.10 (m, 1 H). |
| 10 | n-C$_7$H$_{15}$-C(=O)-N(allyl)-CH(CH$_3$)-naphthyl | 93 | 0.85-0.88 (m, 3 H), 1.26-1.29 (m, 8 H), 1.43-1.70 (m, 5 H), 2.29 (t, 2 H, J = 7.5 Hz), 2.58-3.61 (m, 2H), 4.76-4.80 (m, 2 H), 5.10-5.18 (m, 1 H), 6.69-6.74 (m, 1 H), 7.44-7.55 (m, 4 H), 7.80-7.86 (m, 2 H), 8.01-8.03 (m, 1 H). |
| 11 | n-C$_7$H$_{15}$-C(=O)-N(allyl)-CH(Ph)-CH$_2$-C$_6$H$_4$-CH$_3$ | 94 | 0.87 (t, 3 H, J = 7.3 Hz), 1.23-1.26 (m, 8 H), 1.30 (t, 2 H, J = 6.8 Hz), 1.56-1.58 (m, 2H), 2.17 (t, 2 H, J = 7.1 Hz), 2.27 (s, 3 H), 3.22-3.30 (m, 2 H), 3.61-3.79 (m, 2 H), 4.84-4.95 (m, 2 H), 6.22 (t, 1 H, J = 8.1 Hz), 7.04-7.23 (m, 4 H), 7.28-7.40 (m, 5 H). | proceed at 70° C. for 6 hours. After completion of the reaction, the reaction mixture was added dropwise to 240 ml of 1 N aqueous hydrochloric acid on an ice bath. The resulting mixture was extracted with 300 ml of hexane, and the organic layer was washed with 100 ml of a saturated aqueous solution of sodium chloride and then concentrated under reduced pressure to give 25.0 g of a crude product. The crude product was purified by column chromatography on silica gel (hexane:ethyl acetate=10:1) to give 13.1 g (76%, (1R,2S):(1R,2R)=80:20) of N-[(R)-2-allyloctanoyl]-1-phenylethylamine.

$^1$H-NMR (400 MHz, CDCl$_3$) δ 0.83-0.87 (m, 3H), 1.18-1.23 (m, 8H), 1.42-1.50 (m, 4H), 1.52-1.59 (m, 1H), 2.01-2.06 (m, 1H), 2.14-2.21 (m, 1H), 2.33-2.41 (m, 1H), 4.94-5.20 (m, 3H), 5.60-5.81 (m, 1H), 7.23-7.33 (m, 5H)

EXAMPLES 2 TO 7

The compounds given in Table 3 were obtained in the same manner as in Example 1.

EXAMPLE 8

N-(2-Allyloctanoyl)-(R)-1-(3-methoxyphenyl)ethylamine Diastereomer Purification n-Pentane (25 ml) was added to 1.0 g of an N-(2-allyloctanoyl)-(R)-1-(3-methoxyphenyl)ethylamine diastereomer mixture ((1R,2S):(1R,2R)=77:23), and the mixture was warmed to 40° C. and then allowed to cool slowly to room temperature. The crystalline precipitate was collected by filtration. Thus was obtained 0.47 g (58% recovery upon recrystallization, diastereomer ratio (1R,2S):(1R,2R)=94:6) of the title compound.

TABLE 3

| Example | Compound | Solvent | Yield (%) (Diastereomar ratio) | $^1$H-NMR (400 MHz, CDCl$_3$) |
|---|---|---|---|---|
| 2 | (structure) | THF | 46 (1S, 2R):(1S, 2S) = 72:28 | As described in Example 1 |
| 3 | (structure) | Hexane | 72 (1S, 2R):(1S, 2S) = 82:18 | As described in Example 1 |
| 4 | (structure) | Toluene | 77 (1R, 2S):(1R, 2R) = 81:19 | 0.86-0.86 (m, 3 H), 1.21-1.26 (m, 8 H), 1.45-1.46 (m, 3 H), 1.59-1.67 (m, 2 H), 2.02-2.34 (m, 3 H), 3.79 (s, 3 H), 4.94-5.13 (m, 2 H), 5.59-5.61 (m, 1 H), 5.72-5.76 (m, 1 H), 6.86 (d, 2 H, J = 7.3 Hz), 7.23 (d, 2 H, J = 7.3 Hz) |
| 5 | (structure) | Toluene | 80 (1R, 2S):(1R, 2R) = 77:23 | 0.82-0.86 (m, 3 H), 1.20-1.45 (m, 8 H), 1.43-1.45 (m, 4 H), 1.55-1.62 (m, 1 H), 2.10-2.18 (m, 2 H), 2.34-2.36 (m, 1 H), 3.77 (s, 3 H), 4.93-5.12 (m, 3 H), 5.61-5.76 (m, 1 H), 5.98-6.10 (m, 1 H), 6.77 (d, 1 H, J = 7.1 Hz), 6.85-6.90 (m, 2 H), 7.21-7.24 (m, 1 H). |
| 6 | (structure) | Toluene | 60 (1S, 2R*):(1S, 2S*) = 72:28 | 0.80-0.88 (m, 3 H), 1.15-1.36 (m, 8 H), 1.60-1.75 (m, 5 H), 1.98-2.04 (m, 1 H), 2.16-2.18 (m, 1 H), 2.25-2.38 (m, 1 H), 5.00-5.08 (m, 2 H), 5.72-5.76 (m, 1 H), 5.93-5.95 (m, 1 H), 7.45-7.51 (m, 4 H), 7.79-7.86 (m, 2 H), 8.09-8.11 (m, 1 H). |
| 7 | (structure) | Toluene | 81 (1S, 2R*):(1S, 2S*) = 85:15 | 0.82-0.89 (m, 3 H), 2.14-1.20 (m, 8 H), 1.59 (s, 3 H), 1.99-2.26 (m, 2 H), 2.29 (S, 3 H), 2.96-3.00 (m, 1 H), 3.01-3.11 (m, 1 H), 4.87-4.98 (m, 2 H), 5.26-5.31 (m, 1 H), 5.47-4.57 (m, 1 H), 5.66-5.67 (m, 1 H), 6.96-7.05 (m, 4 H), 7.24-7.52 (m, 5 H). |

EXAMPLE 9

N-(2-Allyloctanoyl)-(S)-1-phenyl-2-(4-methylphenyl)ethylamine diastereomer purification Acetone (6 ml) was added to 1.0 g of an N-(2-allyloctanoyl)-(S)-1-phenyl-2-(4-methylphenyl)ethylamine diastereomer mixture ((1S,2R*):(1S,2S*)=85.3:14.7) and, after dissolution at 50° C., 20 ml of hexane was added, and the resulting mixture was allowed to cool slowly to room temperature. The crystalline precipitate was collected by filtration to give 0.40 g of crystals ((1S,2R*):(1S,2S*)=95.7:4.3). Acetone (4 ml) was added to the crystals obtained and, after dissolution at 50° C., 10 ml of hexane was added, and the resulting mixture was allowed to cool slowly to room temperature. The crystalline precipitate was collected by filtration to give 0.17 g of white crystals (25% recovery upon recrystallization, (1S,2R*):(1S,2S*)=99.3:0.7).

8H), 1.48-1.52 (m, 3H), 1.57-1.69 (m, 3H), 2.22-2.49 (m, 1H), 3.58 (m, 1H), 4.77-4.81 (m, 1H), 4.90-5.19 (m, 2H), 5.68-77 (m, 1H), 5.98-6.02 (m, 1H), 7.20-7.41 (m, 5H).

EXAMPLES 11 TO 14

The following compounds were obtained in the same manner as in Example 10.

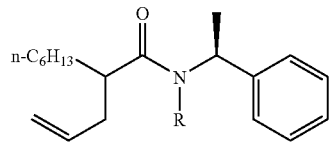

TABLE 4

| Example | R | ClCOOR (amount used; equivalents) | Yield (%) | $^1$H-NMR(400MHz, CDCl$_3$) |
|---|---|---|---|---|
| 11 | COOMe | 3.0 | 86 | 0.88(t, 3H, J=7.3Hz), 1.21-1.29(m, 8H), 1.52-1.55(m, 3H) 1.66(d, 3H, J=6.8Hz), 2.22-2.52(m, 2H), 3.34-3.48(m, 1H) 3.52(s, 3H), 4.97-5.30(m, 2H), 5.66-5.82(m, 1H), 5.97-5.98(m, 1H), 7.21-7.30(m, 5H). |
| 12 | COO-sec-Bu | 1.0 | 54 | 0.54(m, 3H), 0.85-0.94(m, 6H), 1.17-1.49(m, 10H), 1.52-1.67(m, 2H), 1.75-1.80(m, 3H), 2.24-2.56(m, 2H), 3.50-3.65(m, 1H), 4.61-4.68(m, 1H), 4.98-5.17(m, 2H), 5.70-5.85(m, 1H), 6.01-7.20(m, 5H). |
| 13 | COOPh | 2.0 | 94 | 0.85-0.87(m, 3H), 1.26-1.39(m, 8H), 1.55-1.56(m, 2H), 1.78(d, 3H, J=6.8Hz), 2.27-2.31(m, 1H), 2.43-2.50(m, 1H) 3.61-3.64(m, 1H), 5.03-5.10(m, 2H), 5.72-5.86(m, 1H), 6.17-6.20(m, 1H), 7.16-7.44(m, 10H). |
| 14 | COO-4-NO$_2$Ph | 2 | 69 | 0.85-0.87(m, 3H), 1.22-1.36(m, 8H), 1.55-1.57(m, 2H), 1.77(d, 3H, J=6.8Hz), 2.27-2.31(m, 1H), 2.39-2.41(m, 1H), 3.60-3.64(m, 1H), 5.03-5.10(m, 2H), 5.72-5.88(m, 1H), 6.10-6.12(m, 1H), 7.44(d, 2H, J=9.0Hz), 8.33(d, 2H, J=9.0Hz). |

EXAMPLE 10

N-Isopropyloxycarbonyl-N-(2-allyloctanoyl)-(R)-1-phenylethylamine

To a solution of 40.0 g (0.14 mol) of (R)-N-allyl-N-octanoyl-1-phenylethylamine in 400 ml of toluene was added dropwise 105 ml (0.17 mol) of tert-butylmagnesium chloride (1.6 M) at room temperature, and the reaction was allowed to proceed at 70° C. for 6 hours. The reaction mixture was cooled to room temperature and, then, 51.0 g (0.42 mol) of isopropyl chlorocarbonate was added, and the reaction was allowed to proceed at room temperature for 15 hours. After completion of the reaction, the reaction mixture was added dropwise to 170 ml of a 1 N aqueous solution of hydrochloric acid in an ice bath. The reaction mixture was extracted with 400 ml of hexane, and the organic layer was washed with 100 ml of a saturated aqueous solution of sodium chloride and then concentrated under reduced pressure to give 52.1 g of a crude product. The crude product was purified by column chromatography on silica gel (hexane:ethyl acetate=10:1) to give 41.0 g of the title compound as a colorless oil (yield 78%, diastereomer ratio (1R,2S):(1R,2R)=80:20).

$^1$H-NMR (400 MHz, CDCl$_3$) δ 0.72 (d, 3H, J=7.3 Hz), 0.82-0.83 (m, 3H), 1.16 (d, 3H, J=7.3 Hz), 1.18-1.20 (m,

EXAMPLE 15

N-Ethyloxycarbonyl-N-(2-allyloctanoyl)-(R)-1-(3-methoxyphenyl)ethylamine

A solution of 0.40 g (1.3 mmol) of N-(2-allyloctanoyl)-(R)-1-(3-methoxyphenyl)ethylamine (diastereomer ratio (1R,2S):(1R,2R)=77:23) in 2 ml of DMF was added to a solution of 151 mg (3.8 mmol) of sodium hydride in 2 ml of DMF at room temperature, and the reaction was allowed to proceed at 50° C. for 1 hour. To the reaction mixture was added 0.48 ml (5.0 mmol) of ethyl chlorocarbonate, and the mixture was stirred at 50° C. for 12 hours. The reaction mixture was added dropwise to a mixed solution composed of 5 ml of a 1 N aqueous solution of hydrochloric acid and 5 ml of hexane with ice cooling, and the resulting mixture was extracted with two 20-ml portions of hexane. The organic layer was washed with 5 ml of a saturated aqueous solution of sodium chloride and concentrated under reduced pressure to give 0.49 g of a crude product. The crude product was purified on a silica gel column (ethyl acetate:hexane=20:1) to give 0.224 g of the title compound as a colorless oil (yield 46%, (1R,2S):(1R,2R)=77:23).

$^1$H-NMR (400 MHz, CDCl$_3$) δ 0.86-0.88 (m, 3H), 0.98-1.03 (m, 3H), 1.22-1.27 (m, 8H), 1.62-1.68 (m, 2H), 1.81-185 (m, 3H), 2.20-2.55 (m, 2H), 3.52 (m, 1H), 3.78 (s, 3H), 3.82-4.02 (m, 2H), 4.98-5.11 (m, 2H), 5.70-5.76 (m, 1H), 5.83-5.98 (m, 1H), 6.75-6.86 (m, 3H), 7.19-7.26 (m, 1H).

EXAMPLE 16

Methyl 2-allyloctanoate

A solution of 0.345 g (1.0 mmol) of N-methyloxycarbonyl-N-(2-allyloctanoyl)-1-(R)-phenylethylamine in 5 ml of methanol was cooled to 0° C., 0.386 g (2.0 mmol) of NaOMe (28% solution in methanol) was added, and the mixture was stirred for 22 hours. The reaction was terminated by addition of 2 ml of 1 N hydrochloric acid, and the product was extracted with ethyl acetate. The extract was dried over anhydrous sodium sulfate, the solvent was distilled off, and the residue was isolated/purified on a silica gel column to give 0.10 g (51%) of the title compound. N-(2-Allyloctanoyl)-(R)-1-phenylethylamine was formed as a byproduct in 45% yield.

$^1$H-NMR (400 MHz, CDCl$_3$) δ 0.87 (t, 3H, J=6.8 Hz), 1.24-1.28 (m, 8H), 1.54-1.56 (m, 3H), 2.20-2.45 (m, 2H), 3.66 (s, 3H), 4.99-5.04 (m, 2H), 5.68-5.78 (m, 1H).

EXAMPLE 17

Methyl 2-allyloctanoate

A solution of 0.345 g (1.0 mmol) of N-methyloxycarbonyl-N-(2-allyloctanoyl)-1-(R)-phenylethylamine in 5 ml of THF was cooled to 0° C., 0.386 g (2.0 mmol) of NaOMe (28% solution in methanol) was added, and the mixture was stirred for 22 hours. The reaction was terminated by addition of 2 ml of 1 N hydrochloric acid, and the product was extracted with ethyl acetate. The extract was dried over anhydrous sodium sulfate, the solvent was distilled off, and the residue was quantitated by GC. Thus was obtained 0.109 g (55%) of the title compound.

N-(2-Allyloctanoyl)-(R)-1-phenylethylamine was formed as a byproduct in 36% yield.

EXAMPLE 18

Methyl 2-allyloctanoate

A solution of 25.12 g (67.5 mmol) of N-isopropyloxycarbonyl-N-(2-allyloctanoyl)-1-(R)-phenylethylamine ((1R,2S):(1R,2R)=77:23) in 338 ml of THF was cooled to −10° C., 26.1 g (135 mmol) of NaOMe (28% solution in methanol) was added dropwise and, after completion of the addition, the mixture was further stirred for 45 minutes. The reaction was terminated by addition of 120 ml of 1 N hydrochloric acid, and the product was extracted with hexane (100 ml×2). The extract was dried over anhydrous sodium sulfate, and the solvent was distilled off to give 25.90 g of a crude product. This was purified on a silica gel column to give 12.32 g (92%, 54% ee) of the title compound.

EXAMPLE 19

Methyl 2-allyloctanoate

A solution of 40 g (110 mmol) of N-isopropyloxycarbonyl-N-(2-allyloctanoyl)-1-(R)-phenylethylamine ((1R,2S):(1R,2R)=80:20) in 400 ml of hexane was cooled to 0° C., 41.5 g (220 mmol) of NaOMe (28% solution in methanol) was added dropwise and, after completion of the addition, the mixture was further stirred for 5 hours. The reaction was terminated by addition of 230 ml of 1 N hydrochloric acid, and the product was extracted with hexane (400 ml). The organic layer was washed with 100 ml of a saturated aqueous solution of sodium hydrogen carbonate and then with 100 ml of water and dried over anhydrous sodium sulfate, and the solvent was distilled off. The residue was quantitated by GC. Thus was obtained 103.42 g (94%, 60% ee) of the title compound.

EXAMPLE 20

Methyl 2-allyloctanoate

A solution of 0.374 g (1.0 mmol) of N-isopropyloxycarbonyl-N-(2-allyloctanoyl)-1-(R)-phenylethylamine ((1R,2S):(1R,2R)=77.6:22.4) in 5 ml of THF was cooled to 0° C., 0.386 g (2.0 mmol) of NaOMe (28% solution in methanol) was added, and the mixture was stirred for 1 hour. The reaction was terminated by addition of 2 ml of 1 N hydrochloric acid, and the product was extracted with ethyl acetate (30 ml×2). The extract was dried over anhydrous sodium sulfate, and the solvent was distilled off. The residue was quantitated by GC. Thus was obtained 0.165 g (83%, 55.3% ee) of the title compound.

EXAMPLE 21

Methyl 2-allyloctanoate

A solution of 0.374 g (1.0 mmol) of N-isopropyloxycarbonyl-N-(2-allyloctanoyl)-1-(R)-phenylethylamine ((1R,2S):(1R,2R)=77.6:22.4) in 5 ml of THF was cooled to 0° C. A solution of 11 mg (0.2 mmol) of NaOMe in methanol (0.04 g) was added, and the mixture was stirred for 7 hours. The reaction was terminated by addition of 1 ml of 1 N hydrochloric acid, and the product was extracted with ethyl acetate (30 ml×2). The extract was dried over anhydrous sodium sulfate, and the solvent was distilled off. The residue was quantitated by GC. Thus was obtained 0.163 g (82%, 55.0% ee) of the title compound.

EXAMPLE 22

Methyl 2-allyloctanoate

A solution of 0.374 g (1.0 mmol) of N-isopropyloxycarbonyl-N-(2-allyloctanoyl)-1-(R)-phenylethylamine ((1R,2S):(1R,2R)=77.6:22.4) in 5 ml of toluene was cooled to 0° C., 0.386 g (2.0 mmol) of NaOMe (28% solution in methanol) was added, and the mixture was stirred for 21 hours. The reaction was terminated by addition of 2 ml of 1 N hydrochloric acid, and the product was extracted with ethyl acetate (30 ml×2). The extract was dried over anhydrous sodium sulfate, and the solvent was distilled off. The residue was quantitated by GC. Thus was obtained 0.149 g (75%, 54.2% ee) of the title compound.

EXAMPLE 23

Methyl 2-allyloctanoate

A solution of 0.218 g (0.5 mmol) of N-phenyloxycarbonyl-N-(2-allyloctanoyl)-1-(R)-phenylethylamine in 2 ml of methanol was cooled to 0° C., 0.38 g (1.0 mmol) of LiOMe was added, and the mixture was stirred for 22 hours. The reaction was terminated by addition of 2 ml of 1 N hydrochloric acid, and the product was extracted with ethyl acetate (30 ml×2). The extract was dried over anhydrous sodium sulfate, and the solvent was distilled off. The residue was quantitated by GC. Thus was obtained 0.057 g (58%) of the title compound.

EXAMPLE 24

2-Allyloctanoic acid

An aqueous solution of hydrogen peroxide (31% by weight; 0.5 ml, 55.0 mmol) and 0.043 g (1.0 mmol) of lithium hydroxide monohydrate were added dropwise to a solution of 0.20 g (0.50 mmol) of N-ethyloxycarbonyl-N-(2-allyloctanoyl)-(R)-1-(3-methoxyphenyl)ethylamine ((1R,2S):(1R,2R)=77:23) in a mixture of 4 ml of THF and 1 ml of water on an ice bath. The mixture was stirred on an ice bath for 3 hours and then at room temperature for 20 hours. A 2 N aqueous solution of sodium sulfite (5 ml) was added dropwise to the reaction mixture on an ice bath, and the resulting mixture was stirred at room temperature for 2 hours. Water (15 ml) was added to the reaction mixture, and the whole mixture was washed with 5 ml of ethyl acetate. To the aqueous layer was added 2 ml of a 1 N aqueous solution of hydrochloric acid (pH=2), and the resulting mixture was extracted with two 40-ml portions of ethyl acetate. The organic layer was concentrated under reduced pressure to give 0.078 g (83%, 62% ee) of the title compound as a colorless oil.

EXAMPLE 25

2-Allyloctanoic acid

An aqueous solution of hydrogen peroxide (31% by weight; 0.6 ml, 5.6 mmol) and 0.047 g (1.1 mmol) of lithium hydroxide monohydrate were added dropwise to a solution of 0.20 g (0.56 mmol) of N-ethyloxycarbonyl-N-(2-allyloctanoyl)-(R)-1-phenylethylamine (diastereomer ratio (1R,2S):(1R,2R)=81:19) in a mixture of 4 ml of THF and 1 ml of water on an ice bath. The mixture was stirred on an ice bath for 1 hour and then at room temperature for 18 hours. A 2 N aqueous solution of sodium sulfite (10 ml) was added dropwise to the reaction mixture on an ice bath, and the resulting mixture was stirred at room temperature for 1 hour. Water (15 ml) was added to the reaction mixture, and the whole mixture was washed with 5 ml of ethyl acetate. To the aqueous layer was added 6 ml of a 1 N aqueous solution of hydrochloric acid (pH=2), and the resulting mixture was extracted with two 40-ml portions of ethyl acetate. The organic layer was concentrated under reduced pressure to give 0.043 g (42%, 62% ee) of the title compound as a colorless oil.

EXAMPLES 26 TO 43

2-Allyloctanoic acid and methyl 2-allyloctanoate

A 10-mg portion of each of the commercial enzymes specified in Table 5 was weighed in a test tube, 1 ml of 500 mM phosphate buffer (pH 7) and 10 mg of racemic methyl 2-allyloctanoate were added and, after tight closure, shaking was carried out at 30° C. for 26 hours. After completion of the reaction, the reaction mixture was acidified by adding 0.25 ml of 3 M hydrochloric acid and then extracted with 1 ml of ethyl acetate. The ethyl acetate phase was analyzed by gas chromatography, and the degree of conversion, the optical purity of the product, 2-allyloctanoic acid, and the optical purity of the remaining substrate, methyl 2-allyloctanoate were determined. The results are shown in Table 5.

TABLE 5

| Example | Enzyme | Manufacturer | Source | Degree of conversion (%) | Optical purity of the product | | Optical purity of Remaining substrate | |
|---|---|---|---|---|---|---|---|---|
| | | | | | (% e.e.) | Absolute configuration | (% e.e.) | Absolute configuration |
| 26 | Novozym CALB L | Novozymes Japan Ltd. | *Candida antarctica* | 22 | 98 | S | 28 | R |
| 27 | Lipase SP525 | Novozymes Japan Ltd. | *Candida antarctica* | 54 | 68 | S | 80 | R |
| 28 | Lipase OF | Meito Sangyo Co., Ltd. | *Candida cylindracea* | 90 | 6 | R | 54 | S |
| 29 | Lipase (Type VII) | Sigma Co. | *Candida cylindracea* | 52 | 24 | S | 26 | R |
| 30 | Lipase L-049 | Biocatalysts Limited | *Candida lipolitica* | 87 | 14 | R | 94 | S |
| 31 | Lipase AYS | Amano Enzyme Inc. | *Candida rugosa* | 94 | 3 | R | 47 | S |
| 32 | Lipase L-053 | Biocatalysts Limited | *Humicola lanuginosa* | 13 | 53 | R | 8 | S |
| 33 | Lipase SP523 | Novozymes Japan Ltd. | *Humicola* sp. | 12 | 58 | R | 8 | S |
| 34 | Lipase L-166P | Biocatalysts Limited | *Mucor javanicus* | 90 | 10 | R | 90 | S |
| 35 | Lipozyme 10000L | Novozymes Japan Ltd. | *Mucor meihei* | 59 | 34 | R | 49 | S |
| 36 | Lipase SP388 | Novozymes Japan Ltd. | *Mucor miehei* | 60 | 37 | R | 56 | S |
| 37 | Lipase WO 2-12 | Boehringer Mannheim GmbH | *Pseuedomonas* sp. | 7 | 76 | S | 6 | R |
| 38 | Lipase D | Amano Enzyme Inc. | *Rhizopus delemar* | 63 | 6 | R | 10 | S |
| 39 | Lipase L-058 | Biocatalysts Limited | *Rhizopus delemar* | 32 | 12 | R | 6 | S |
| 40 | Lipase Saiken 50 | Nagase Chemtex Corporation | *Rhizopus javanicus* | 68 | 14 | R | 30 | S |
| 41 | Lipase | Seikagaku Corporation | *Rhizopus delemar* | 96 | 1 | R | 24 | S |
| 42 | Olipase 4S | Osaka Saikin Kenkyusho | *Rhizopus javanicus* | 33 | 10 | R | 5 | S |
| 43 | Lipase D | Amano Enzyme Inc. | *Rhizopus delemar* | 89 | 3 | R | 24 | S |

EXAMPLES 44 TO 61

2-Allyloctanoic acid and ethyl 2-allyloctanoate

Racemic ethyl 2-allyloctanoate was subjected to the same procedure as in Examples 26 to 43, and the degree of conversion, the optical purity of the product, 2-allyloctanoic acid, and the optical purity of the remaining substrate, ethyl 2-allyloctanoate were determined. The results are shown in Table 6.

TABLE 6

| Example | Enzyme | Manufacturer | Source | Degree of conversion (%) | Optical purity of the product (% e.e.) | Absolute configuration | Optical purity of Remaining substrate (% e.e.) | Absolute configuration |
|---|---|---|---|---|---|---|---|---|
| 44 | Novozym CALB L | Novozymes Japan Ltd. | *Candida antarctica* | 33 | 96 | S | 47 | R |
| 45 | Lipase SP525 | Novozymes Japan Ltd. | *Candida antarctica* | 58 | 65 | S | 90 | R |
| 46 | Lipase OF | Meito Sangyo Co., Ltd. | *Candida cylindracea* | 95 | 4 | R | 76 | S |
| 47 | Lipase (Type VII) | Sigma Co. | *Candida cylindracea* | 57 | 36 | S | 48 | R |
| 48 | Lipase L-049 | Biocatalysts Limited | *Candida lipolitica* | 96 | 1 | R | 24 | S |
| 49 | Lipase AYS | Amano Enzyme Inc. | *Candida rugosa* | 90 | 10 | S | 90 | R |
| 50 | Lipase L-053 | Biocatalysts Limited | *Humicola lanuginosa* | 2 | 66 | R | 1 | S |
| 51 | Lipase SP523 | Novozymes Japan Ltd. | *Humicola* sp. | 38 | 63 | R | 39 | S |
| 52 | Lipase L-166P | Biocatalysts Limited | *Mucor javanicus* | 91 | 4 | R | 40 | S |
| 53 | Lipozyme 10000L | Novozymes Japan Ltd. | *Mucor meihei* | 92 | 1 | R | 12 | S |
| 54 | Lipase SP388 | Novozymes Japan Ltd. | *Mucor miehei* | 77 | 11 | R | 37 | S |
| 55 | Lipase WO 2-12 | Boehringer Mannheim GmbH | *Pseudomonas* sp. | 6 | 92 | S | 6 | R |
| 56 | Lipase D | Amano Enzyme Inc. | *Rhizopus delemar* | 82 | 0 |  | 0 |  |
| 57 | Lipase L-058 | Biocatalysts Limited | *Rhizopus delemar* | 53 | 5 | R | 6 | S |
| 58 | Lipase Saiken 50 | Nagase Chemtex Corporation | *Rhizopus javanicus* | 71 | 10 | R | 24 | S |
| 59 | Lipase | Seikagaku Corporation | *Rhizopus delemar* | 68 | 2 | R | 4 | S |
| 60 | Olipase 4S | Osaka Saikin Kenkyusho | *Rhizopus javanicus* | 38 | 20 | R | 12 | S |
| 61 | Lipase D | Amano Enzyme Inc. | *Rhizopus delemar* | 95 | 4 | R | 76 | S |

EXAMPLES 62 TO 77

2-Allyloctanoic acid and methyl 2-allyloctanoate

A medium (pH 7.0) comprising 1% of polypeptone, 1% of meat extract, 0.5% of yeast extract and 0.3% of sodium chloride was distributed in 5-ml portions into test tubes and, after sterilization, seeded respectively with the microorganisms specified in Table 7. Shake culture was performed aerobically at 30° C. for 2 days. Cells were collected from each culture fluid by centrifugation and suspended in 1 ml of 500 mM phosphate buffer (pH 7.0). A 5-mg portion of racemic methyl 2-allyloctanoate was added to the suspension and, after tight closure, shaking was carried out at 30° C. for 15 hours. After the reaction, the reaction mixture was acidified by addition of 0.25 ml of 3 M hydrochloric acid and then extracted with 1 ml of ethyl acetate. The ethyl acetate phase was analyzed by gas chromatography, and the degree of conversion, the optical purity of the product, 2-allyloctanoic acid and the optical purity of the remaining substrate, methyl 2-allyloctanoate were determined. The results thus obtained are shown in Table 7.

TABLE 7

| Example | Microorganism | Degree of conversion (%) | Optical purity of the product (% e.e.) | Absolute configuration | Optical purity of Remaining substrate (% e.e.) | Absolute configuration |
|---|---|---|---|---|---|---|
| 62 | *Brevundimonas diminuta* IFO 13181 | 14 | 50 | S | 8 | R |
| 63 | *Brevundimonas diminuta* IFO 13182 | 13 | 47 | S | 7 | R |
| 64 | *Cellulomonas fimi* IFO15513 | 60 | 46 | S | 69 | R |
| 65 | *Jensenia canicruria* IFO 13914 | 42 | 96 | S | 70 | R |
| 66 | *Rhodococcus erythropolis* IFO 12320 | 44 | 92 | S | 72 | R |
| 67 | *Rhodococcus erythropolis* IFO 12538 | 30 | 87 | S | 38 | R |
| 68 | *Rhodococcus erythropolis* IFO 12539 | 30 | 85 | S | 37 | R |
| 69 | *Rhodococcus erythropolis* IAM 1474 | 17 | 62 | S | 13 | R |
| 70 | *Rhodococcus erythropolis* IFO 12320 | 41 | 84 | S | 58 | R |
| 71 | *Rhodococcus erythropolis* JCM 3132 | 33 | 88 | S | 44 | R |
| 72 | *Rhodococcus erythropolis* IAM 1440 | 36 | 87 | S | 49 | R |
| 73 | *Rhodococcus erythropolis* IAM 1452 | 37 | 84 | S | 50 | R |
| 74 | *Rhodococcus erythropolis* IAM 1463 | 36 | 90 | S | 51 | R |
| 75 | *Rhodococcus erythropolis* IAM 1494 | 25 | 66 | S | 22 | R |
| 76 | *Rhodococcus erythropolis* IAM 1474 | 21 | 67 | S | 18 | R |
| 77 | *Rhodococcus erythropolis* IAM 12122 | 15 | 75 | S | 13 | R |

EXAMPLES 78 TO 81

2-Allyloctanoic acid and methyl 2-allyloctanoate

Using the microorganisms listed in Table 8, the procedure of Examples 62 to 77 was repeated in the same manner except that a medium (pH 6.5) comprising 2% of malt extract, 2% of glucose, 0.3% of peptone and 0.3% of yeast extract was used, and the degree of conversion, the optical purity of the product, 2-allyloctanoic acid and the optical purity of the remaining substrate, methyl 2-allyloctanoate were determined in each run. The results obtained are shown in Table 8.

TABLE 8

| Example | Microorganism | Degree of conversion (%) | Optical purity of the product | | Optical purity of Remaining substrate | |
|---|---|---|---|---|---|---|
| | | | (% e.e.) | Absolute configuration | (% e.e.) | Absolute configuration |
| 78 | *Candida pini* IFO 1327 | 30 | 90 | R | 39 | S |
| 79 | *Saccharomycopsis selenospora* IFO 1850 | 18 | 82 | R | 18 | S |
| 80 | *Trichosporon cutaneum* IFO 1198 | 13 | 71 | S | 10 | R |
| 81 | *Trichosporon debeurmannianum* CBS 1896 | 19 | 94 | R | 22 | S |

EXAMPLE 82

2-Allyloctanoic acid and methyl 2-allyloctanoate

In a flask, there were placed 50 ml of 100 mM phosphate buffer (pH 6.0), 6 g of Novozyme CALB L (product of Novozyms) and 2 g of methyl (S)-2-allyloctanoate (60% ee) prepared in Example 31. After tight closure, the flask was shaken at 40° C. for 77 hours. To the mixture was added 0.35 ml of a 55% (w/w) aqueous solution of sulfuric acid, and the resulting mixture was extracted with two 100-ml portions of ethyl acetate. The organic phases were combined, and the product was transferred to 100 ml of a 0.3 M aqueous solution of sodium carbonate. Furthermore, 5 ml of a 55% (w/w) aqueous solution of sulfuric acid was added to that aqueous phase, followed by extraction with 50 ml of ethyl acetate. The organic phase was washed with 50 ml of water, and the solvent was then distilled off to give 1.21 g of (S)-2-allyloctanoic acid (99% ee). The organic phase remaining after the transfer of the reaction product to the 100 ml portion of the 0.3 M aqueous solution of sodium carbonate was washed with 50 ml of water, and the solvent was then distilled off to give 0.63 g of methyl (R)-2-allyloctanoate (14% ee).

INDUSTRIAL APPLICABILITY

As described hereinabove, it is possible to produce an optically active 2-allylcarboxylic acid derivative, which is useful as an intermediate for the manufacture of medicinal compounds, and the like, from readily available and inexpensive starting materials by the process which can be practiced on a commercial scale in a simple and easy manner. Furthermore, certain 2-allylcarboxamide derivative compounds, which are novel and important intermediates in that process, can be provided.

The invention claimed is:
1. A process for producing an optically active 2-allylcarboxylic acid represented by the following formula (5);

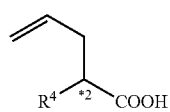

(5)

wherein $R^4$ represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms and *2 indicates that the carbon atom marked therewith is an asymmetric carbon atom;
which comprises:
(a) reacting a carboxamide compound represented by the following formula (2);

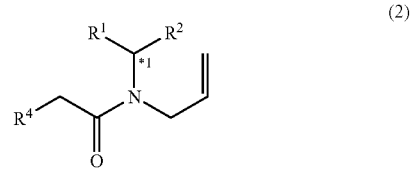

(2)

wherein $R^1$ and $R^2$ each independently represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms, $R^4$ is as defined above and *1 indicates that the carbon atom marked therewith is an asymmetric carbon atom;
with an organometallic compound and then further with a compound represented by the formula;

ClCOOR$^5$ wherein $R^5$ represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms;
to give a 2-allylcarboxamide derivative represented by the following formula (3);

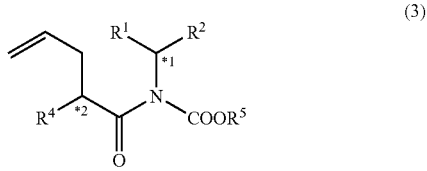

(3)

wherein $R^1$, $R^2$, $R^4$, $R^5$, *1 and *2 are as defined above;
(b) reacting the derivative (3) with a compound represented by the formula MOR$^6$ wherein M represents an alkali metal and $R^6$ represents a substituted or unsubstituted alkyl group containing 1 to 20 carbon atoms to give a 2-allylcarboxylic acid ester derivative represented by the following formula (4);

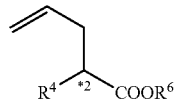
(4)

wherein $R^4$, $R^6$ and *2 are as defined above; and (c) further hydrolyzing the derivative (4).

2. The process according to claim 1,
wherein an organomagnesium compound is used as the organometallic compound.

3. The process according to claim 2,
wherein a tert-butylmagnesium halide is used as the organomagnesium compound.

4. The process according to claim 3,
wherein tert-butylmagnesium chloride is used as the tert-butylmagnesium halide.

5. The process according to claim 1,
wherein $R^5$ is phenyl group.

6. The process according to claim 1,
wherein $R^5$ is isopropyl group.

7. The process according to claim 1,
wherein M is a sodium atom.

8. The process according to claim 1,
wherein $R^6$ is methyl group.

9. The process according to claim 1,
wherein the step (b) is carried out in the presence of not less than 1.0 mole, per mole of the compound represented by the formula (3), of $R^6OH$.

10. The process according to claim 1,
wherein the compound represented by the formula (2) is in an optically active form.

11. The process according to claim 1,
wherein the hydrolysis in step (c) is carried out using an enzyme source capable of causing asymmetric hydrolysis.

12. The process according to claim 11,
wherein the enzyme source is an enzyme source derived from a microorganism belonging to the genus *Candida, Humicola, Mucor, Pseudomonas, Rhizopus, Brevundimonas, Cellulomonas, Jensenia, Rhodococcus, Saccharomycopsis* or *Trichosporon*.

13. The process according to claim 11,
wherein the enzyme source is an enzyme source derived from *Candida antarctica, Candida lipolitica, Candida cylindracea, Candida rugosa, Humicola* sp., *Humicola lanuginosa, Mucor meihei, Mucor javanicus, Pseudomonas* sp., *Rhizopus delemar, Rhizopus javanicus, Brevundimonas diminuta, Cellulomonas fimi, Jensenia canicruria, Rhodococcus erythropolis, Candida pini, Saccharomycopsis selenospora, Trichosporon cutaneum* or *Trichosporon debeurmannianum*.

14. A process for producing a 2-allylcarboxamide derivative represented by the following formula (3);

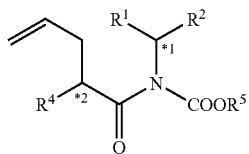
(3)

wherein $R^1$, $R^2$, $R^4$ and $R^5$ each independently represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms, and *1 and *2 each indicates that the carbon atom marked therewith is an asymmetric carbon atom;

which comprises reacting a compound represented by the following formula (6);

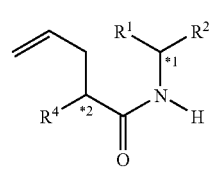
(6)

wherein $R^1$, $R^2$, $R^4$, *1 and *2 are as defined above;
in the presence of a base and further with a compound represented by the formula;

ClCOOR⁵ wherein $R^5$ is as defined above.

15. The process according to claim 14,
wherein an alkali metal compound or an alkaline earth metal compound is used as the base.

16. The process according to claim 15,
wherein sodium hydride is used as the alkali metal compound.

17. The process according to claim 15,
wherein an organomagnesium compound is used as the alkaline earth metal compound.

18. The process according to claim 17,
wherein a tert-butylmagnesium halide is used as the organomagnesium compound.

19. The process according to claim 18,
wherein tert-butylmagnesium chloride is used as the tert-butylmagnesium halide.

20. The process according to claim 14,
wherein $R^5$ is phenyl group.

21. The process according to claim 14,
wherein $R^5$ is isopropyl group.

22. A process for producing a 2-allylcarboxamide derivative represented by the following formula (3);

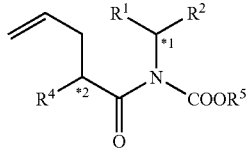
(3)

wherein $R^1$, $R^2$, $R^4$ and $R^5$ each independently represents a substituted or unsubstituted alkyl group containing 1 to 18 carbon atoms, a substituted or unsubstituted aryl group containing 6 to 20 carbon atoms or a substituted or unsubstituted aralkyl group containing 7 to 20 carbon atoms, and *1 and *2 each indicates that the carbon atom marked therewith is an asymmetric carbon atom;

which comprises reacting a carboxamide compound represented by the following formula (2);

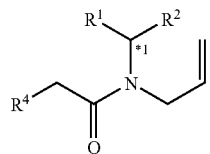

(2)

wherein $R^1$, $R^2$, $R^4$ and *1 are as defined above;

with an organometallic compound and further with a compound represented by the formula;

ClCOOR$^5$ wherein $R^5$ is as defined above.

23. The process according to claim 22, wherein an organomagnesium compound is used as the organometallic compound.

24. The process according to claim 23, wherein a tert-butylmagnesium halide is used as the organomagnesium compound.

25. The process according to claim 24, wherein tert-butylmagnesium chloride is used as the tert-butylmagnesium halide.

26. The process according to claim 22, wherein $R^5$ is phenyl group.

27. The process according to claim 22, wherein $R^5$ is isopropyl group.

* * * * *